(12) United States Patent
Yasutomi et al.

(10) Patent No.: US 11,494,696 B2
(45) Date of Patent: *Nov. 8, 2022

(54) LEARNING APPARATUS, LEARNING METHOD, AND RECORDING MEDIUM

(71) Applicant: FUJITSU LIMITED, Kawasaki (JP)

(72) Inventors: Suguru Yasutomi, Kawasaki (JP); Kento Uemura, Kawasaki (JP); Takashi Katoh, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 421 days.

This patent is subject to a terminal disclaimer.

(21) Appl. No.: 16/717,563

(22) Filed: Dec. 17, 2019

(65) Prior Publication Data

US 2020/0226494 A1 Jul. 16, 2020

(30) Foreign Application Priority Data

Jan. 11, 2019 (JP) .............................. JP2019-003849

(51) Int. Cl.
*G06T 7/00* (2017.01)
*G06N 20/00* (2019.01)
(Continued)

(52) U.S. Cl.
CPC ........... *G06N 20/00* (2019.01); *A61B 8/5207* (2013.01); *A61B 8/5246* (2013.01); *G06F 17/18* (2013.01);
(Continued)

(58) Field of Classification Search
CPC .... G06N 20/00; G06N 3/02; G06N 3/08–088; G06N 3/0454; A61B 8/5207;
(Continued)

(56) References Cited

U.S. PATENT DOCUMENTS 9,965,901 B2 5/2018 Zhang et al.
10,387,765 B2 8/2019 Mailhe et al.
(Continued)

OTHER PUBLICATIONS

Notice of Allowance, dated May 14, 2021, in U.S. Appl. No. 16/720,667 (12 PP).
(Continued)

*Primary Examiner* — Jose L Couso
(74) *Attorney, Agent, or Firm* — Staas & Halsey LLP

(57) ABSTRACT

A non-transitory computer-readable recording medium stores therein a learning program that causes a computer to execute a process including: generating a shadow image including a shadow according to a state of ultrasound reflection in an ultrasound image; generating a combined image by combining the ultrasound image and the shadow image; inputting, into a first decoder and a second decoder, an output acquired from an encoder in response to inputting the combined image into the encoder; and executing training of the encoder, the first decoder, and the second decoder, based on: reconfigured error between an output image of a coupling function and the combined image, the coupling function being configured to combine a first image output from the first decoder with a second image output from the second decoder, and an error function between an area in the first image and the shadow in the shadow image.

5 Claims, 9 Drawing Sheets

(51) Int. Cl.
*A61B 8/08* (2006.01)
*G06F 17/18* (2006.01)
*G06T 5/50* (2006.01)

(52) U.S. Cl.
CPC ...... *G06T 5/50* (2013.01); *G06T 2207/10132* (2013.01); *G06T 2207/20076* (2013.01); *G06T 2207/20212* (2013.01)

(58) Field of Classification Search
CPC ......... A61B 8/5246; A61B 8/00; A61B 8/085; A61B 8/46; A61B 8/52; A61B 8/5269; A61B 2090/378; A61B 8/0825; A61B 8/0875; A61B 8/0891; G06F 17/18; G06T 5/50; G06T 2207/10132; G06T 2207/20076; G06T 2207/20212; G06T 2207/20081; G06T 2207/20084; G06T 2207/30004; G06T 7/0012; G06T 2207/10136; G06T 11/008; G06T 2210/41; G06T 5/001; G06T 5/002; G06T 5/003; G06T 7/002; G06T 2207/30068; G06T 2207/30101; G06T 2207/10081; G06T 2207/10001; G06T 2207/30061; G06V 40/1306; G06V 10/44; G06V 10/454; G06V 10/46; G06V 10/462; G06V 10/82; G06V 30/194; G06V 2201/03; G06K 7/02; G06K 9/6256; G06K 9/6267; G06K 9/6271; G16H 50/20; G16H 30/40; G16H 30/20

See application file for complete search history.

(56) References Cited

U.S. PATENT DOCUMENTS

| | | |
|---|---|---|
| 10,430,688 B2 | 10/2019 | Rao et al. |
| 10,698,063 B2 | 6/2020 | Braun et al. |
| 10,702,242 B2 | 7/2020 | de Jonge et al. |
| 10,852,379 B2 | 12/2020 | Chen et al. |
| 11,100,678 B2 * | 8/2021 | Yasutomi ................ G06T 9/002 |
| 2018/0330518 A1 | 11/2018 | Choi |
| 2019/0000425 A1 * | 1/2019 | Hu ........................ G06T 7/0012 |
| 2019/0142380 A1 * | 5/2019 | Emery ................. A61B 8/4483 600/439 |
| 2019/0142390 A1 * | 5/2019 | Luo ........................ G06N 3/02 600/437 |
| 2019/0295295 A1 * | 9/2019 | Hyun ...................... G06N 3/08 |
| 2020/0226796 A1 | 7/2020 | Yasutomi et al. |

OTHER PUBLICATIONS

Cerrolaza Juan J. et al.; "Deep learning with ultrasound physics for fetal skull segmentation"; 2018 IEEE 15th International Symposium on Biomedical Imaging (ISBI 2018), IEEE, Apr. 4, 2018, pp. 564-567, XP033348264, DOI: 10.1109/ISBI.2018.8363639 [retrieved on May 23, 2018]; (4 pages).

Li Yan et al.; "Automatic fetal body and amniotic fluid segmentation from fetal ultrasound images by encoder-decoder network with inner layers"; 2017 39th Annual International Conference of the IEEE Engineering in Medicine and Biology Society (EMBC), IEEE, Jul. 11, 2017, pp. 1485-1488, XP033152327, DOI: 10.1109/EMBC.2017.8037116 [retrieved on Sep. 13, 2017]; (4 pages).

Extended European Search Report dated Mar. 18, 2020 in European Patent Application No. 19215565.3 (9 pages).

Hellier, Pierre, et al., "An automatic geometrical and statistical method to detect acoustic shadows in intraoperative ultrasound brain images.", Medical Image Analysis (vol. 14), pp. 195-204, Apr. 12, 2010.

Qingjie, Meng et al., "Automatic Shadow Detection in 2D Ultrasound", 1st Conference on Medical Imaging with Deep Learning, 2018, p. 1-3.

Adiga, Sukesh V. et al., *Shared Encoder based Denoising of Optical Coherence Tomography Images*, 11th Indian Conference on Computer Vision, Graphics and Image Processing (ICVGIP-2018), Dec. 2018, XP055688876 (9 pp.).

Gibson, Eli et al., *NiftyNet: a deep-learning platform for medical imaging*, arxiv.org, Cornell University Library, 201 Olin Library, Cornell University, Ithaca, NY 14853, Sep. 11, 2017 (Sep. 11, 2017), XP081294865 (26 pp.).

Meng, Qingjie et al. *Automatic Shadow Detection in 2D Ultrasound Images*, International Conference on Financial Cryptography and Data Security; [Lecture Notes in Computer Science], Springer, Berlin, Heidelberg, Sep. 15, 2018 (Sep. 15, 2018) pp. 66-75, XP047485755 (10 pp.).

Extended European Search Report, dated May 8, 2020, in European Application No. 19217485.2 (9 pp.).

Office Action, dated Jan. 25, 2021, in U.S. Appl. No. 16/720,667 (16 pp.).

U.S. Appl. No. 16/720,667, filed Dec. 19, 2019, Suguru Yasutomi, Fujitsu Limited.

* cited by examiner

LEARNING APPARATUS, LEARNING METHOD, AND RECORDING MEDIUM

CROSS-REFERENCE TO RELATED APPLICATION

This application is based upon and claims the benefit of priority of the prior Japanese Patent Application No. 2019-003849, filed on Jan. 11, 2019, the entire contents of which are incorporated herein by reference.

FIELD

The embodiments discussed herein are related to machine learning technology.

BACKGROUND

Object detection and state determination by image processing using ultrasound images have been done for medical diagnoses and non-destructive inspection of structures. A model, such as a deep neural net (DNN), which has been trained by machine learning, is used in such image processing of ultrasound images.

Ultrasound images may have shadows appearing therein due to difference in transmission speed of ultrasound among substances and reflection of ultrasound. In this case, image processing thereon will be reduced in accuracy. Proposed against this reduction in accuracy is a technique for rule-based determination of presence of any shadow in an ultrasound image having a specific part of a human body captured therein.

For example, related arts are disclosed in Hellier, Pierre, et al., "An automatic geometrical and statistical method to detect acoustic shadows in intraoperative ultrasound brain images," Medical Image Analysis 14.2 (2010): 195-204.

SUMMARY

According to an aspect of the embodiments, a non-transitory computer-readable recording medium stores therein a learning program that causes a computer to execute a process including: generating a shadow image including a shadow according to a state of ultrasound reflection in an ultrasound image; generating a combined image by combining the ultrasound image and the shadow image; inputting, into a first decoder and a second decoder, an output acquired from an encoder in response to inputting the combined image into the encoder; and executing training of the encoder, the first decoder, and the second decoder, based on: reconfigured error between an output image of a coupling function and the combined image, the coupling function being configured to combine a first image output from the first decoder with a second image output from the second decoder, an error function between an area in the first image and the shadow in the shadow image, the area corresponding to the shadow in the shadow image, and a likelihood function related to a likelihood of the second image with respect to an object in the ultrasound image.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

The above-mentioned conventional technique has a problem that versatility of the determination of presence of any shadow in an ultrasound image may be reduced. For example, the above-mentioned conventional technique is not versatile as rules and a determination model need to be prepared for each part of a human body.

Preferred embodiments will be explained with reference to accompanying drawings. The present invention is not limited by these embodiments. Furthermore, the embodiments may be combined as appropriate without causing contradictions.

Described first of all is an embodiment of the present invention. A model according to the embodiment is based on an autoencoder using a DNN, and has one encoder and two decoders that are a shadow decoder and a target decoder. Furthermore, this model has a coupling function that combines outputs from the two decoders. The shadow decoder is an example of a first decoder. Furthermore, the object decoder is an example of a second decoder.

Figure 1:
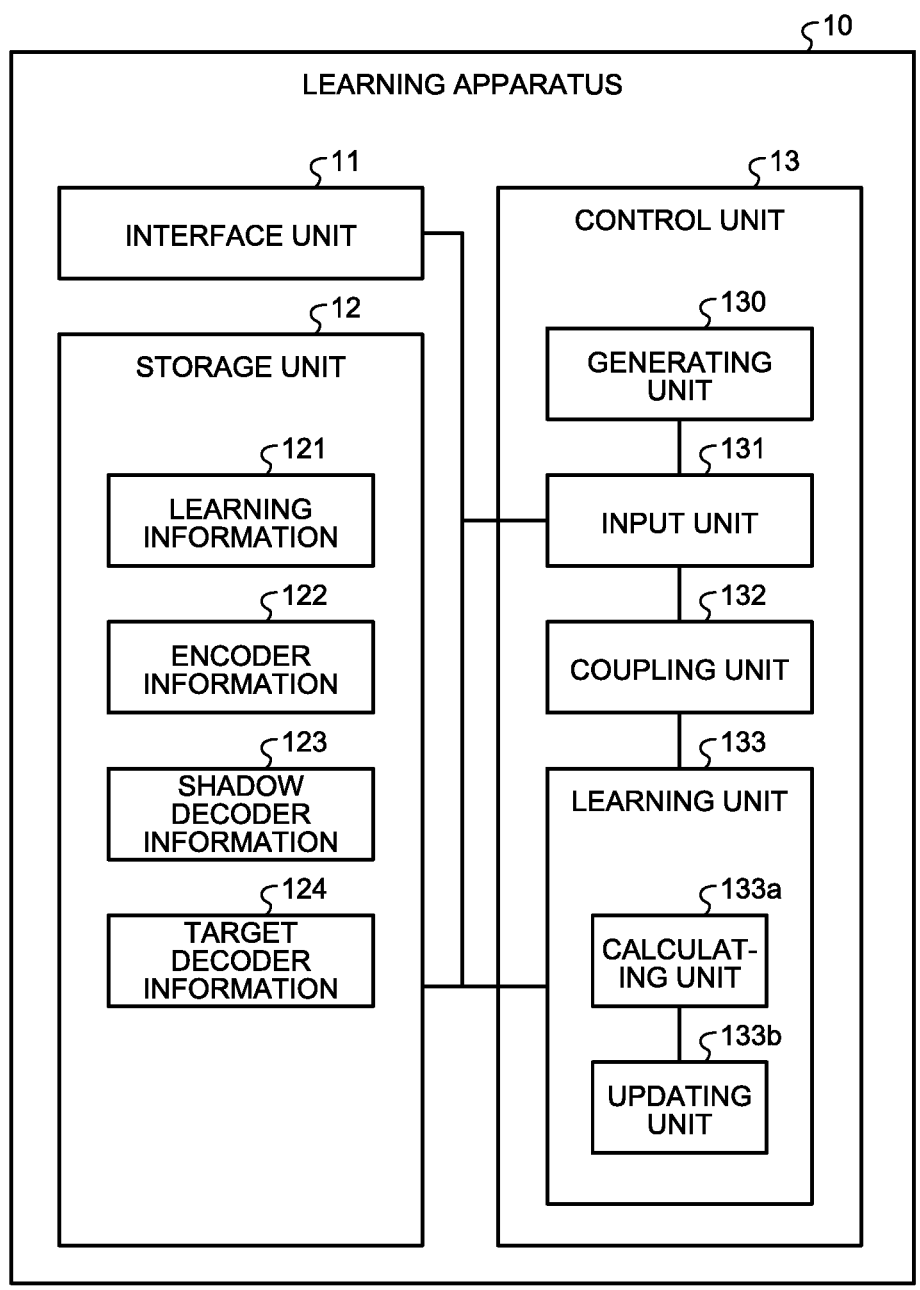
FIG. 1 is a diagram illustrating an example of a functional configuration of a learning apparatus according to an embodiment.

A functional configuration of a learning apparatus according to the embodiment will be described by use of FIG. 1. FIG. 1 is a diagram illustrating an example of the functional configuration of the learning apparatus according to the embodiment. As illustrated in FIG. 1, a learning apparatus 10 has an interface unit 11, a storage unit 12, and a control unit 13.

The interface unit 11 is an interface for performing input and output of data from and to an input and output device, and for performing communication of data with another device. For example, the interface unit 11 performs input and output of data from or to: an input device, such as a keyboard or a mouse; an output device, such as a display or a speaker; and an external storage device, such as a USB memory. Furthermore, for example, the interface unit 11 is a network interface card (NIC), and performs communication of data via the Internet.

The storage unit 12 is an example of a storage device that stores therein data and a program that is executed by the control unit 13; and is, for example, a hard disk or a memory. The storage unit 12 stores therein learning information 121, encoder information 122, shadow decoder information 123, and target decoder information 124.

The learning information 121 is information, such as a hyperparameter used upon training of the model. For example, the learning information 121 includes a learning rate, a batch size, and a distribution parameter of a likelihood function.

The encoder information 122 includes a parameter of the encoder. Furthermore, the shadow decoder information 123 includes a parameter of the shadow decoder. Moreover, the target decoder information 124 includes a parameter of the target decoder. Learnable parameters of the encoder and the decoders will hereinafter be called model parameters. For example, the model parameters include weight and bias of the DNN. In addition, the encoder information 122, the shadow decoder information 123, and the target decoder information 124 are updated upon training of the model.

The control unit 13 is realized by, for example, a program being executed by a central processing unit (CPU), a micro processing unit (MPU), or a graphics processing unit (GPU), with a RAM serving as a work area, the program having been stored in an internal storage device. Furthermore, the control unit 13 may be realized by, for example, an integrated circuit, such as an application specific integrated circuit (ASIC) or a field programmable gate array (FPGA). The control unit 13 has a generating unit 130, an input unit 131, a coupling unit 132, and a learning unit 133. Moreover, the learning unit 133 has a calculating unit 133a and an updating unit 133b.

The generating unit 130 generates a shadow image including a shadow corresponding to a state of ultrasound reflection in an input ultrasound image. The generating unit 130 generates an image of only the shadow by a predetermined technique. In the following description, the shadow generated by the generating unit 130 will be called the generated shadow, and an image including the generated shadow will be called a generated shadow image. Trends of shape and position of a shadow generated in an input ultrasound image actually generated by use of a probe differ according to a state of ultrasound reflection based on a shape of the probe. Therefore, the generating unit 130 generates a generated shadow image according to a state of ultrasound reflection.

The input unit 131 inputs an output from the encoder, into which a combined image has been input, to the shadow decoder and the target decoder, the combined image being a combination of an input ultrasound image and a generated shadow image. Furthermore, the coupling unit 132 combines an image of shadow with an image of target by using a coupling function, the image of shadow being an output from the shadow decoder, the image of target being an output from the target decoder. The image of shadow is an example of a first image. The image of target is an example of a second image.

Based on reconfigured error, an error function, and a likelihood function, the learning unit 133 executes training of the encoder, the shadow decoder, and the target decoder. The reconfigured error is reconfigured error between: an output image of the coupling function that combines the image of shadow with the image of target, the image of shadow being an output from the shadow decoder, the image of target being an output from the target decoder; and the combined image. The error function is an error function between: an area in the image of shadow, the area corresponding to the shadow in the generated shadow image; and the shadow in the generated shadow image. The likelihood function is a likelihood function for the image of target, the likelihood function being related to a target in an ultrasound image.

The calculating unit 133a calculates a loss function from: the reconfigured error, error of shadow based on the error function, and likelihood based on the likelihood function. Furthermore, the updating unit 133b updates the model parameters of the encoder, the shadow decoder, and the target decoder, such that the value of the error function is decreased. Specifically, the updating unit 133b updates the encoder information 122, the shadow decoder information 123, and the target decoder information 124.

Figure 2:
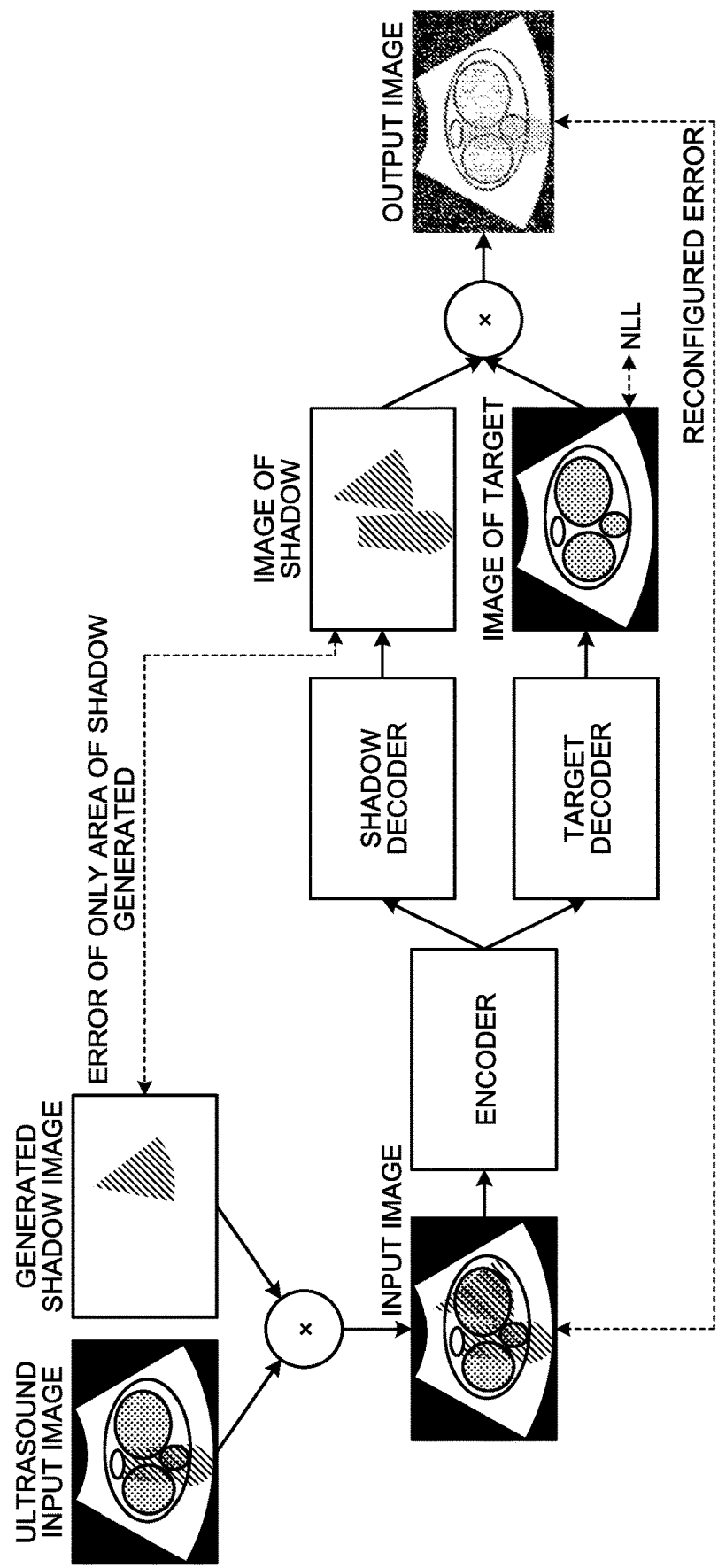
FIG. 2 is a diagram illustrating learning processing.

Learning processing by the learning apparatus 10 will now be described by use of FIG. 2. FIG. 2 is a diagram illustrating the learning processing. As illustrated in FIG. 2, the input unit 131 inputs an input image into the encoder.

An input ultrasound image in FIG. 2 is an ultrasound image of the interior of a human body, the ultrasound image having been acquired by use of a medical probe. In the following description, an image resulting from visualization of a signal acquired from the probe will be called an ultrasound image. It is assumed that in ultrasound images, a part where a target that reflects ultrasound is present is displayed brightly, the target being, for example, an organ. On the contrary, it is assumed that a shadow appearing in an ultrasound image is displayed darkly.

For example, the speed, at which ultrasound is transmitted inside a human body is about the same as the speed, at which ultrasound is transmitted in water, but when air is present in an imaged region upon imaging of the interior of a human body, it becomes difficult for ultrasound to be transmitted and a shadow may be generated in an ultrasound image. The input ultrasound image in FIG. 2 is an ultrasound image captured by application of ultrasound to a target from an upper side in FIG. 2. Furthermore, a hatched portion of the input ultrasound image is a shadow.

The generating unit 130 generates a generated shadow image. As illustrated in FIG. 2, the generated shadow image is an image having a shadow arranged in a part of an area of a frame having the same size as the input ultrasound image. The generating unit 130 may generate the generated shadow image by any technique.

Figure 3:
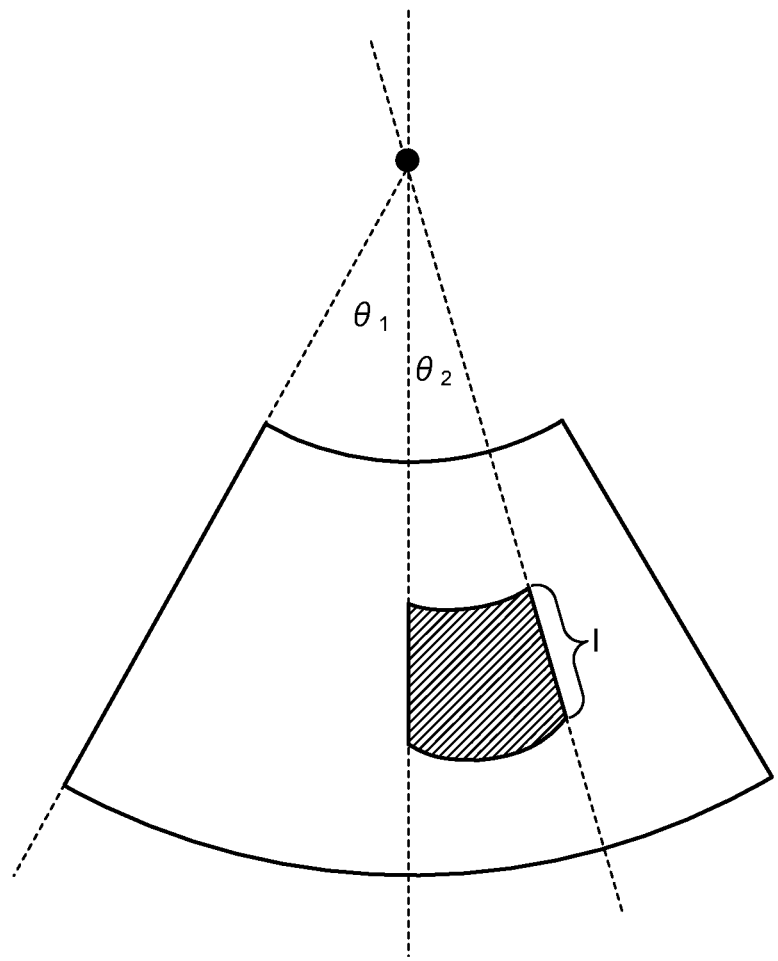
FIG. 3 is a diagram illustrating generation of a shadow image.

Described now by use of FIG. 3 is a method of generating a generated shadow image. FIG. 3 is a diagram illustrating generation of a shadow image. An area surrounded by a solid line in FIG. 3 represents a region imaged by the probe. The generating unit 130 generates a shadow in a hatched area in FIG. 3. The generating unit 130 may determine the hatched area by randomly determining "$\theta_1$", "$\theta_2$", and "l".

The shape of the imaged region differs according to the type of the probe. For example, if the probe is of the convex type, the shape of the imaged region forms a part of a fan shape as illustrated in FIG. 3. Furthermore, if the probe is of the linear type, the imaged region becomes rectangular. The generating unit 130 may generate a shadow by setting an imaged region according to the type of the probe. The generating method described above is just an example, and the generating unit 130 may generate a generated shadow image by another method.

The input unit 131 generates an input image by combining an input ultrasound image with a generated shadow image. The input ultrasound image is represented by pixel values respectively set for pixels thereof. The pixel values are values indicating brightness, and are expressed by numerical values respectively for the pixels, the numerical values being in a range of, for example, 0 to 255 (8-bit). On the contrary, the generated shadow image is represented by numerical values (hereinafter, shadow numerical values), "1" in a part without a shadow and numerical values in a range of [0,1) in a part with the shadow. By multiplying the pixel values in the input ultrasound image by the shadow numerical values in the generated shadow image, an image is thus able to be generated, the image having the input ultrasound image with a darkened portion corresponding to the shadow in the generated shadow image. Furthermore, the input unit 131 inputs the input image into the encoder.

The input unit 131 inputs an output from the encoder, into which the input image has been input, into the shadow decoder and the target decoder. That is, if the encoder is a neural network having a first layer with a predetermined number of nodes and a last layer having less nodes than the first layer, this last layer is connected to a first layer of each of the decoders, which are also neural networks.

The shadow decoder and the target decoder output images. By the number of nodes in a last layer of each of the decoders being made equal to the number of nodes in the first layer of the encoder, each of the decoders is able to be caused to output an image having the same size as the input image.

As illustrated in FIG. 2, the coupling unit 132 generates an output image by combining an image of target with an image of shadow by using a coupling function that multiplies these images together. As learning progresses, the shadow decoder will start to output an image represented by numerical values, "1" for a part without a shadow and numerical values in a range of [0,1) for a part with the shadow, similarly to the generated shadow image. The target decoder, on the other hand, will start to output an image represented by pixel values of scales equivalent to those of the input ultrasound image.

For example, if a shadow numerical value of a pixel at coordinates (i,j) in an image of shadow is $p_{ij}$, and a pixel value of the pixel at the coordinates (i,j) in the image of shadow is $q_{ij}$, the coupling unit 132 may calculate a pixel value $r_{ij}$ of a pixel at coordinates (i,j) in an output image as "$r_{ij}=p_{ij} \cdot q_{ij}$".

The calculating unit 133a calculates reconfigured error between the input image and the output image combined by the coupling unit 132. The calculating unit 133a may calculate the reconfigured error by a technique similar to that by a known autoencoder.

Furthermore, the calculating unit 133a calculates error between the image of shadow output by the shadow decoder, and the generated shadow image. In this calculation, the calculating unit 133a uses, as the error function, the square error between the shadow numerical values of corresponding pixels in these images. However, the calculating unit 133a calculates the error only for the area where the shadow has been arranged in the generated shadow image.

Figure 4:
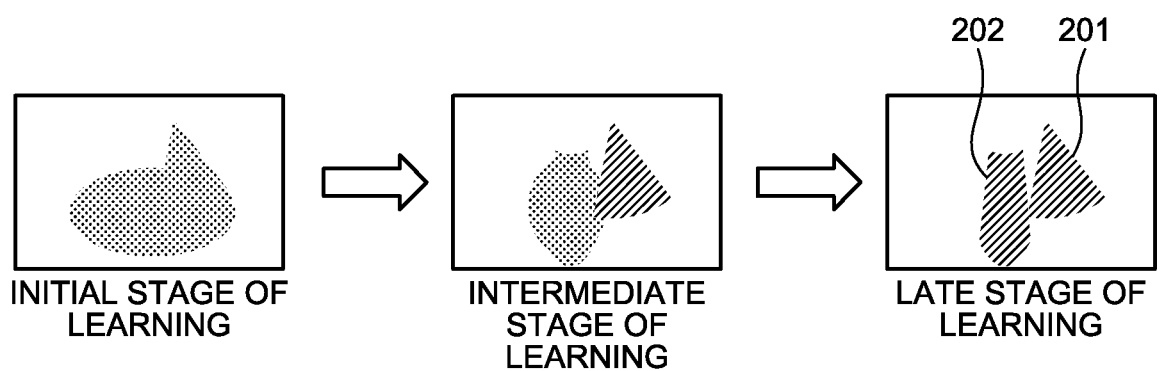
FIG. 4 is a diagram illustrating progress of learning.

As learning progresses, images of shadow output by the shadow decoder change as illustrated in FIG. 4. FIG. 4 is a diagram illustrating the progress of learning. As illustrated in FIG. 4, at an initial stage of the learning, a shadow corresponding to both a generated shadow and an actually generated shadow appears unclearly. At an intermediate stage of the learning, the shadow corresponding to both the generated shadow and the actually generated shadow starts to become somewhat clear. Furthermore, at a late stage of the learning, it is able to be clearly confirmed that a shadow corresponding to the generated shadow is being displayed in an area 201, and a shadow corresponding to the actually generated shadow is being displayed in an area 202. However, the calculating unit 133a calculates error for the area 201 but does not calculate error for the area 202. The learning undergoes transition among the initial stage, the intermediate stage, and the late stage, every time update of the model parameters is performed a certain number of times.

Figure 5:
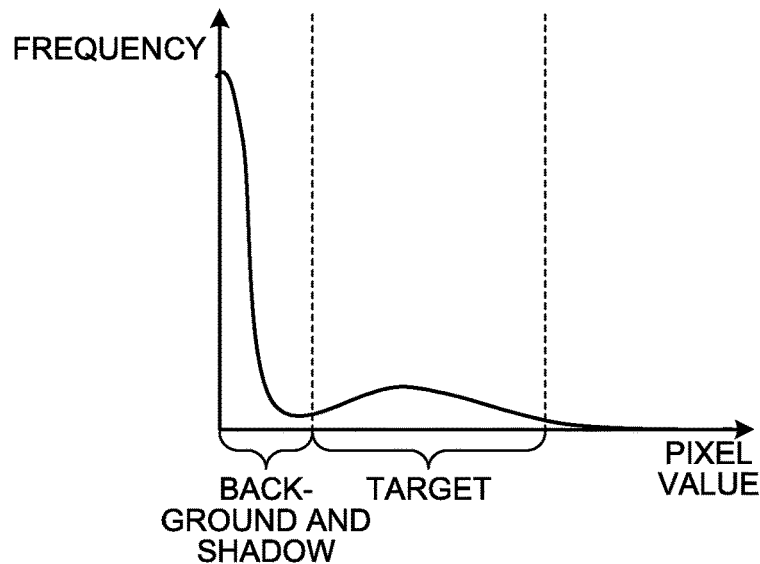
FIG. 5 is a diagram illustrating an example of a histogram of an ultrasound image.

Furthermore, the calculating unit 133a calculates a negative log likelihood (NLL) as a likelihood of the image of target. In this calculation, the calculating unit 133a uses, as the likelihood function, a function having a variable representing a value corresponding to a pixel value of the image, the function having a maximum value for the variable corresponding to a predetermined pixel value that is neither a maximum pixel value nor a minimum pixel value. This is because, as illustrated in FIG. 5, in an ultrasound image, a target is displayed comparatively brightly as compared to a shadow and the background, and a mountain corresponding to the target is formed on a histogram thereof. FIG. 5 is a diagram illustrating an example of the histogram of the ultrasound image.

Specifically, the calculating unit 133a uses a likelihood function based on a probability density function of beta distribution having parameters set such that the probability density function has a maximum value when a random variable corresponding to a pixel value of an image is at a predetermined value larger than 0 and smaller than 1. The probability density function of beta distribution is expressed by Equation (1). In Equation (1), B($\alpha$, $\beta$) is a beta function. Furthermore, $\alpha$ and $\beta$ are parameters determining the distribution profile of the beta distribution.

$$p(x \mid \alpha, \beta) = \frac{x^{\alpha-1}(1-x)^{\beta-1}}{B(\alpha, \beta)} \qquad (1)$$

Figure 6:
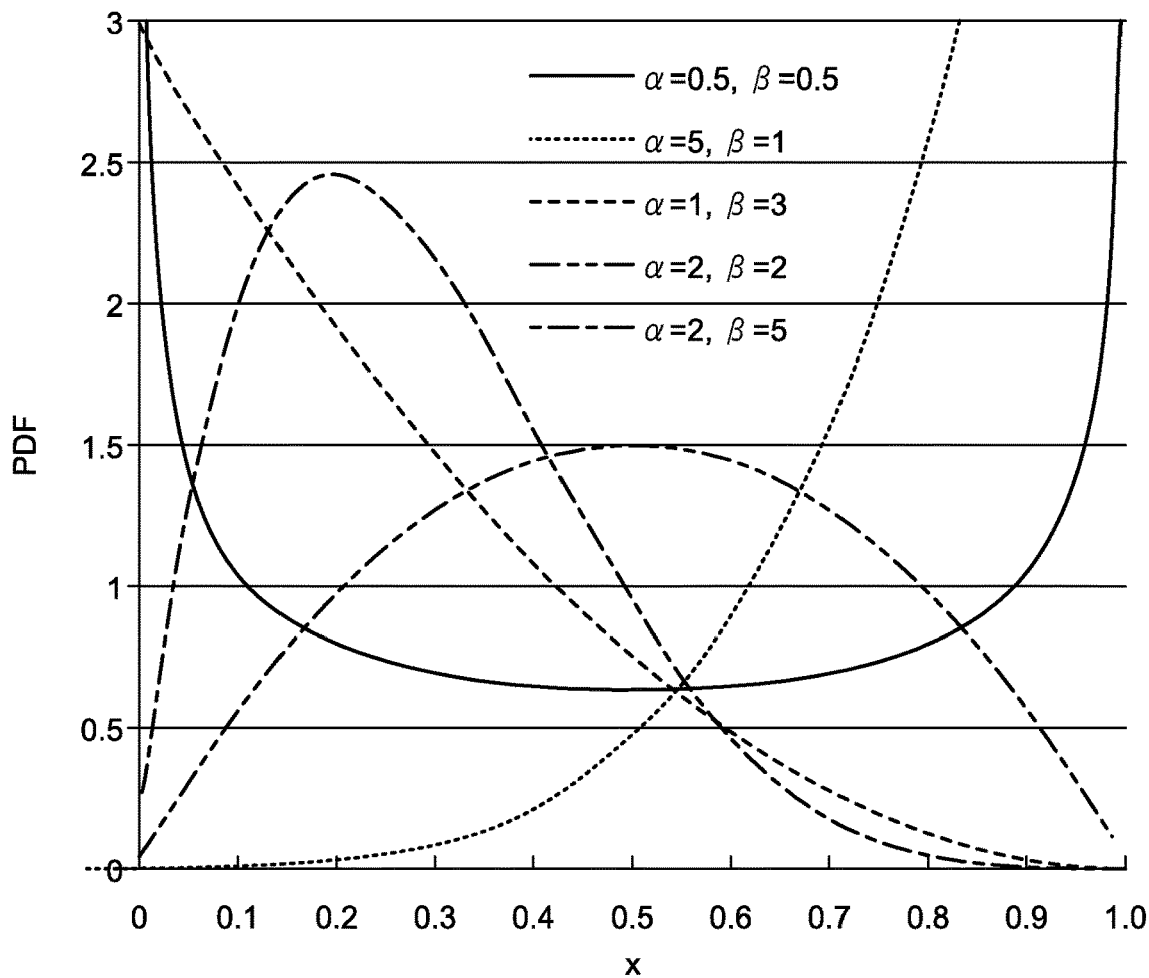
FIG. 6 is a diagram illustrating beta distributions.

Profiles of beta distributions according to $\alpha$ and $\beta$ will be described by use of FIG. 6. FIG. 6 is a diagram illustrating beta distributions. As illustrated in FIG. 6, for example, in a case where "$\alpha=0.5$" and "$\beta=0.5$", the probability density function (PDF) has a maximum value when the random variable x is 0 or 1. Furthermore, in a case where, for example, "$\alpha=2$" and "$\beta=5$", the PDF has a maximum value when the random variable x is about 0.2.

Among the combinations of values of $\alpha$ and $\beta$ in FIG. 6, combinations that satisfy the condition, "having a maximum value when a random variable corresponding to a pixel value of an image is at a predetermined value larger than 0 and smaller than 1", are "$\alpha=2$ and $\beta=2$", and "$\alpha=2$ and $\beta=5$". Therefore, the calculating unit 133a may use, as likelihood functions, for example, the probability density function of beta distribution where the combination, "$\alpha=2$ and $\beta=2$", has been set, and the probability density function of beta distribution where the combination, "$\alpha=2$ and $\beta=5$", has been set. Effective set values for $\alpha$ and $\beta$ are not limited to the ones described above, and may be any set values satisfying the condition.

Even if pixel values of an image output from the target decoder are represented in a range of 0 to 255, by performing normalization by multiplying the pixel values by 1/255, the calculating unit 133a may make the normalized pixel values become a random variable of 0 to 1.

Specifically, the calculating unit 133a calculates an NLL of an image output from the target decoder as expressed by Equation (2). In Equation (2), $p(x_m \mid \alpha, \beta)$ is a probability density function of beta distribution in Equation (1). Furthermore, values satisfying the condition as described above are set for α and β. Moreover, "m" in Equation (2) is an index indicating each pixel in the image. Furthermore, $x_m$ is a normalized pixel value of a pixel m.

$$NLL = -\log \prod_m p(x_m | \alpha, \beta) = -\sum_m \log p(x_m | \alpha, \beta) \quad (2)$$

The calculating unit 133a calculates, as the loss function, a linear sum of error in the image of shadow, the NLL of the image of target, and configuration error between the output image and the input image. For example, the calculating unit 133a calculates the loss function as "$W_1$×(the configuration error)+$W_2$×(error in the image of shadow)+$W_3$×(NLL of the image of target)". $W_1$, $W_2$, and $W_3$ are preset weights, and may be included in the learning information 121 as hyperparameters. Furthermore, $W_1$, $W_2$, and $W_3$ may be set such that they are all positive and satisfy, "$W_1+W_2+W_3=1$".

The updating unit 133b updates the model parameters of the encoder, the shadow decoder, and the target decoder, such that the value of the error function is decreased. For example, the updating unit 133b updates the model parameters by using the back propagation method.

Figure 7:
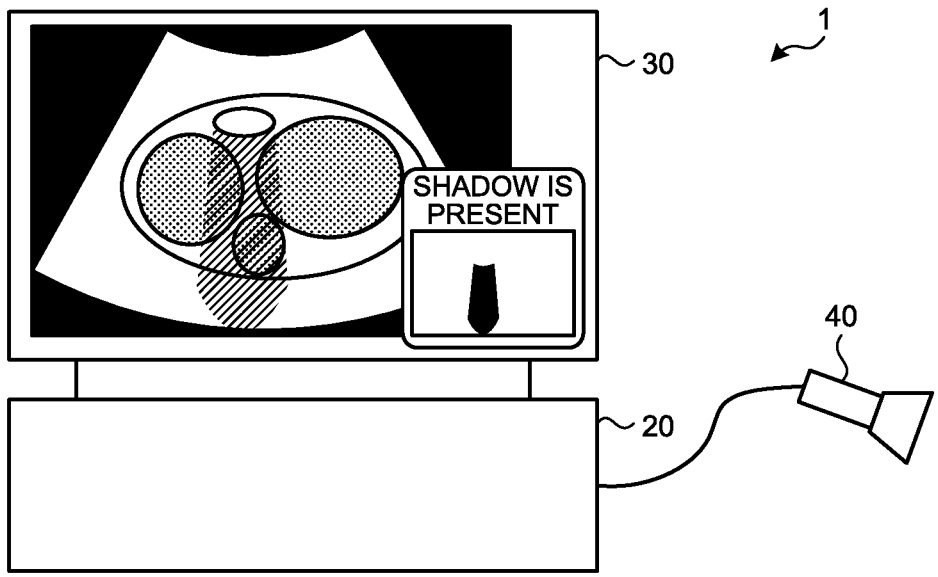
FIG. 7 is a diagram illustrating an example of an image processing system according to an embodiment.

An image processing system may perform image processing by using the encoder and shadow decoder that have been trained in the learning apparatus 10. This image processing system will be described by use of FIG. 7. FIG. 7 is a diagram illustrating an example of the image processing system according to an embodiment.

As illustrated in FIG. 7, an image processing system 1 has a recognition apparatus 20, a display device 30, and a probe 40. The recognition apparatus 20 performs, based on a signal received from the probe 40, generation of an ultrasound image and predetermined postprocessing, and outputs the generated ultrasound image and a result of the postprocessing, to the display device 30. The probe 40 generates ultrasound, and receives ultrasound that has been reflected. Furthermore, the probe 40 may generate an ultrasound image, and transmit the generated ultrasound image, to the recognition apparatus 20.

The image processing system 1 is used in diagnoses by doctors. For example, the probe 40 is put on a body surface of a patient by a doctor, and transmits, as a signal, ultrasound that the probe 40 has received, to the recognition apparatus 20. The recognition apparatus 20 causes the display device 30 to display an ultrasound image generated based on the signal received from the probe 40. Furthermore, the recognition apparatus 20 determines presence of any shadow in the ultrasound image, and performs postprocessing according to the presence of any shadow.

The recognition apparatus 20 may perform, as the postprocessing, processing of notifying the doctor, via the display device 30 or another output device, of a fact that a shadow appears in the ultrasound image. Furthermore, as illustrated in FIG. 7, the recognition apparatus 20 may cause the display device 30 to display a generated image of shadow. Moreover, the recognition apparatus 20 may combine the ultrasound image with the image of shadow, and generate an image having the ultrasound image, from which a shadow has been removed.

In the postprocessing, the recognition apparatus 20 determines, based on the presence of any shadow in the ultrasound image, whether or not predetermined image recognition is applicable to the ultrasound image, and if the predetermined image recognition is applicable to the ultrasound image, the recognition apparatus 20 performs image recognition. The image recognition includes, for example, object detection and state determination.

Figure 8:
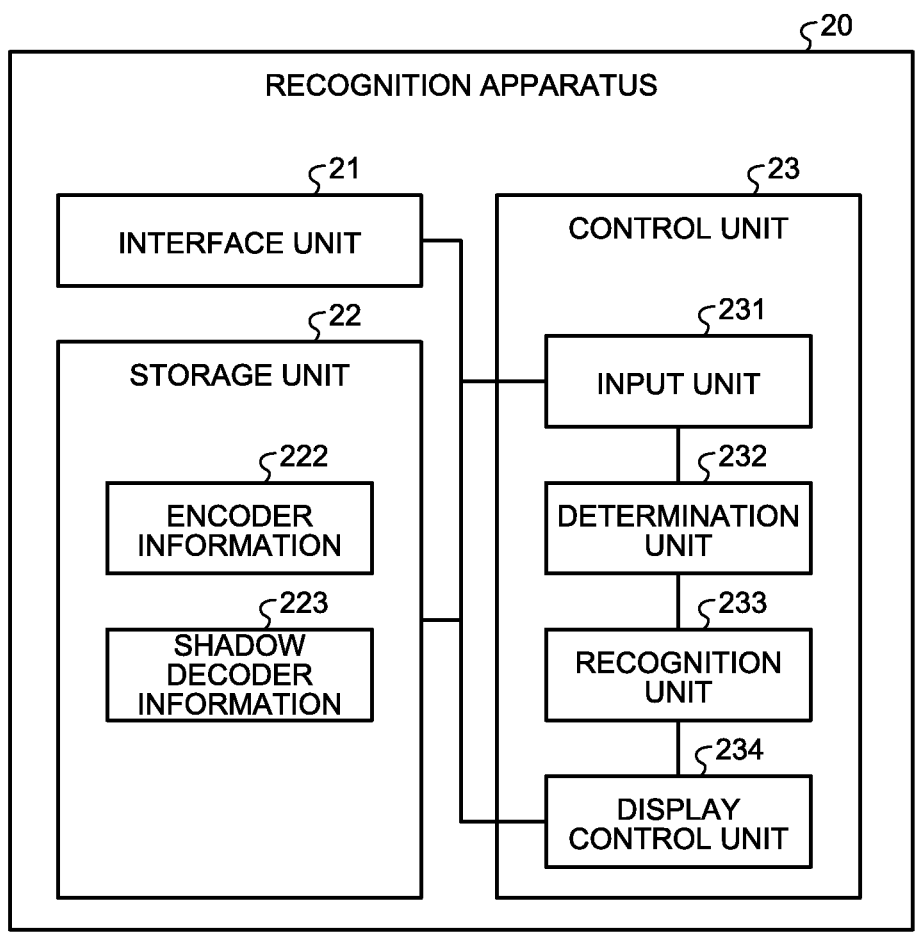
FIG. 8 is a diagram illustrating an example of a functional configuration of a recognition apparatus according to the embodiment.

Described by use of FIG. 8 is a functional configuration of the recognition apparatus 20 according to the embodiment. FIG. 8 is a diagram illustrating an example of the functional configuration of the recognition apparatus 20 according to the embodiment. As illustrated in FIG. 8, the recognition apparatus 20 has an interface unit 21, a storage unit 22, and a control unit 23.

The interface unit 21 is an interface for performing input and output of data from and to an input and output device, and communication of data with another device. For example, the interface unit 21 performs input and output of data from and to the display device 30 and probe 40.

The storage unit 22 is an example of a storage device that stores therein data and a program executed by the control unit 23, and is, for example, a hard disk or a memory. The storage unit 22 stores therein encoder information 222 and shadow decoder information 223.

The encoder information 222 is data similar to the encoder information 122 after learning has been performed in the learning apparatus 10. Furthermore, the shadow decoder information 223 is data similar to the shadow decoder information 123 after learning has been performed in the learning apparatus 10. Therefore, by using the encoder information 222 and shadow decoder information 223, the recognition apparatus 20 is able to construct an encoder and a shadow decoder that have been trained.

The control unit 23 is realized by, for example, a program being executed by a CPU, an MPU, or a GPU, with a RAM being a work area, the program having been stored in an internal storage device. Furthermore, the control unit 23 may be realized by, for example, an integrated circuit, such as an ASIC or FPGA. The control unit 23 has an input unit 231, a determination unit 232, a recognition unit 233, and a display control unit 234.

The input unit 231 performs processing similar to that by the input unit 131 of the learning apparatus 10. That is, the input unit 231 inputs an output from the encoder, into which an input image has been input, into the shadow decoder. Furthermore, the determination unit 232 determines, based on an image of shadow, whether or not image recognition is applicable to the input image. The recognition unit 233 executes image recognition when image recognition is determined to be applicable. Moreover, the display control unit 234 causes the display device 30 to display an ultrasound image. In addition, the display control unit 234 may cause the display device 30 to display results of determination processing by the determination unit 232 and image recognition by the recognition unit 233.

Figure 9:
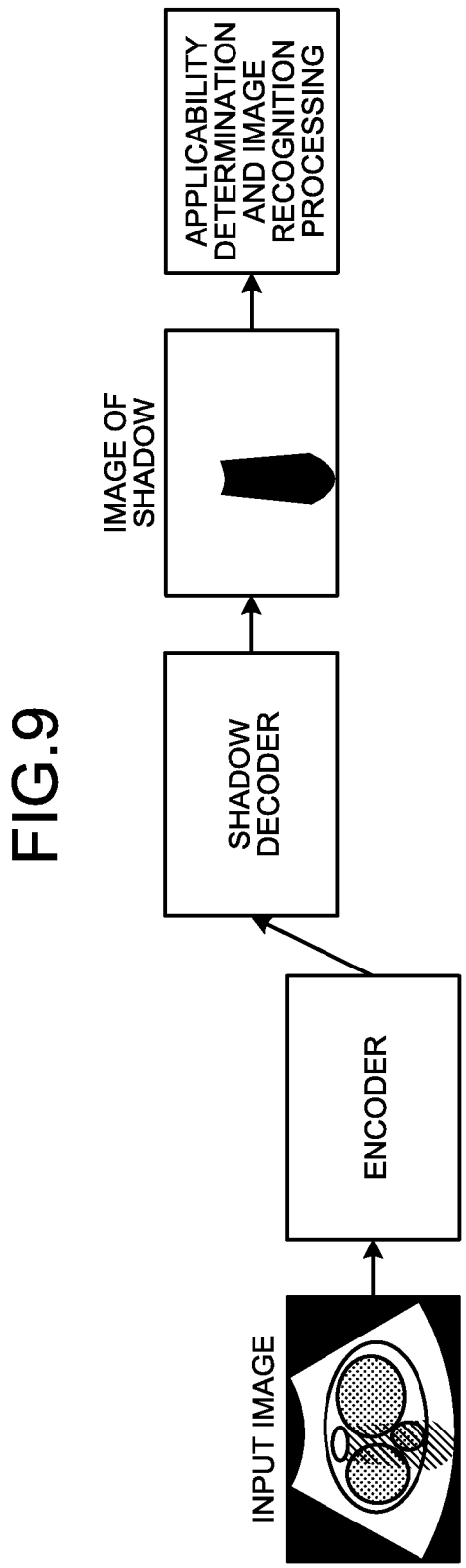
FIG. 9 is a diagram illustrating recognition processing.

Described now by use of FIG. 9 is recognition processing by the recognition apparatus 20. FIG. 9 is a diagram illustrating the recognition processing. As illustrated in FIG. 9, the input unit 231 inputs an input image into the encoder. This input image in FIG. 9 is an ultrasound image acquired by use of the probe 40.

The input unit 231 inputs an output from the encoder, into which the input image has been input, into the shadow decoder. Based on an image of shadow output by the shadow decoder, the recognition apparatus 20 then performs, image recognition applicability determination and image recognition processing. For example, the determination unit 232 determines that a shadow is present if the total of shadow numerical values of pixels of the image of shadow is equal to or less than a threshold.

Figure 10:
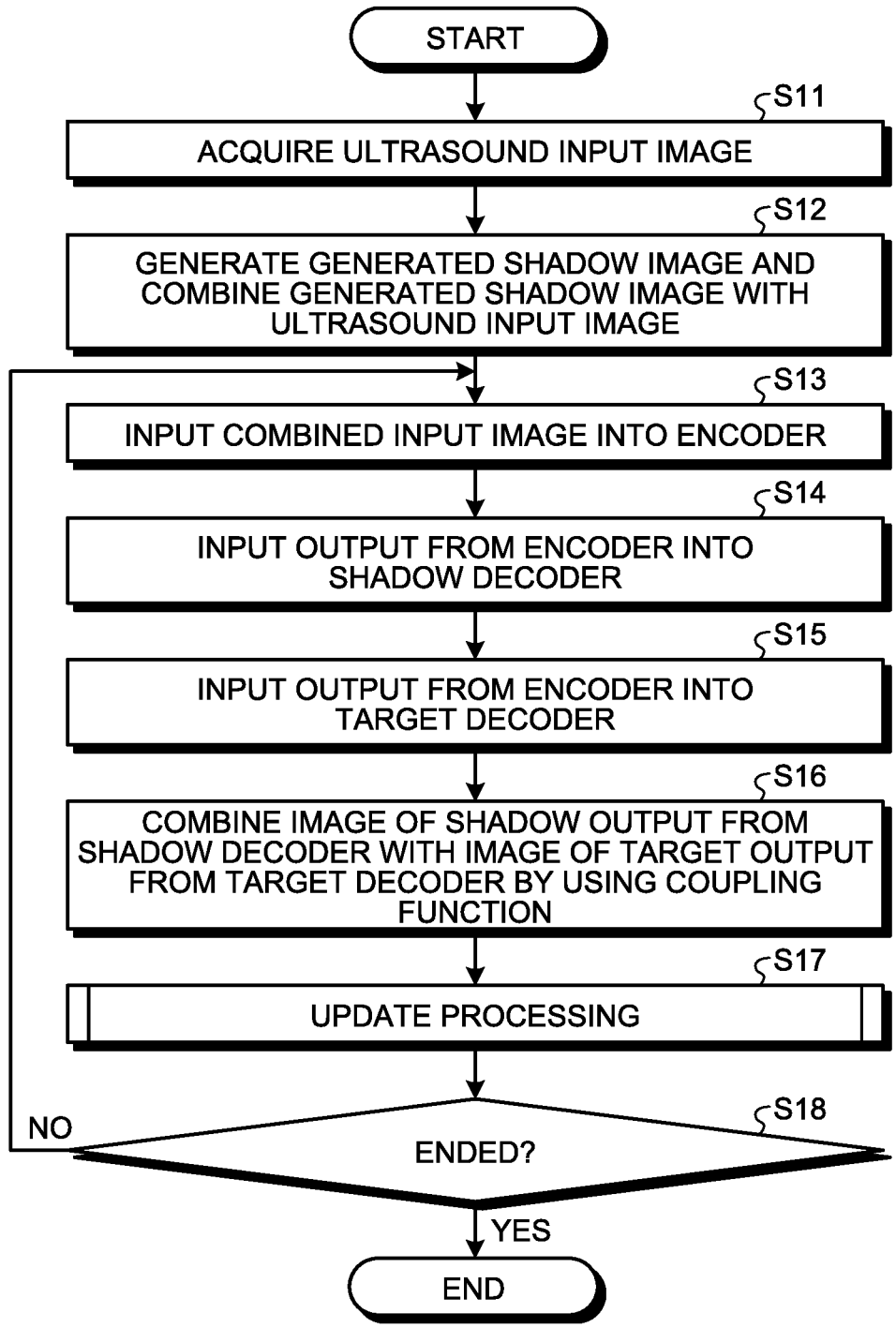
FIG. 10 is a flow chart illustrating a flow of the learning processing.

Described now by use of FIG. 10 is a flow of learning processing by the learning apparatus 10. FIG. 10 is a flow chart illustrating the flow of learning processing. As illustrated in FIG. 10, firstly, the learning apparatus 10 acquires an input ultrasound image (Step S11). Furthermore, the learning apparatus 10 generates a generated shadow image, and combines the generated shadow image with the input ultrasound image (Step S12).

The learning apparatus 10 inputs an input image generated, into the encoder (Step S13). Subsequently, the learning apparatus 10 inputs an output from the encoder, into the shadow decoder (Step S14), and inputs an output from the encoder, to the target decoder (Step S15).

The learning apparatus 10 combines an image of shadow output from the shadow decoder, with an image of target output from the target decoder, by using a coupling function (Step S16). The learning apparatus 10 then performs update processing for the model parameters (Step S17), and determines whether or not the update processing has ended (Step S18).

If the learning apparatus 10 determines that the update processing has ended (Step S18; Yes), the learning apparatus 10 ends the learning processing. On the contrary, if the learning apparatus 10 determines that the update processing has not ended (Step S18; No), the learning apparatus 10 returns to Step S13 and repeats the processing. For example, the learning apparatus 10 determines that the update processing has ended, if the update processing has been performed a preset number of times, or if the amount of update of the model parameters has become equal to or less than a threshold.

Figure 11:
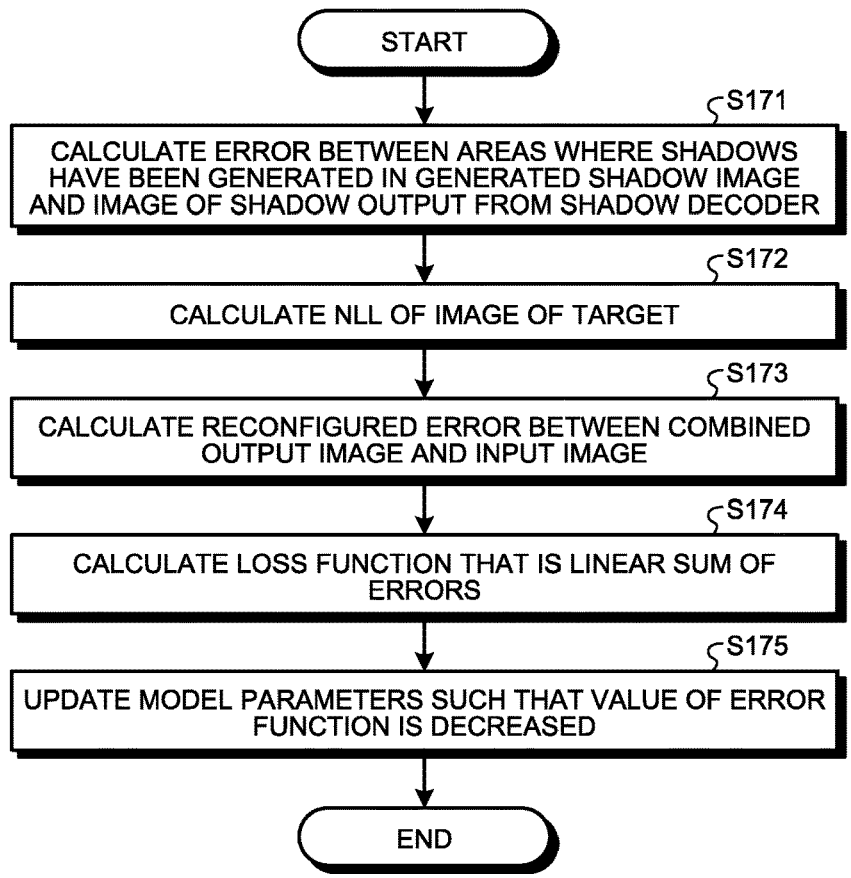
FIG. 11 is a flow chart illustrating a flow of update processing.

A flow of the update processing at Step S17 will now be described by use of FIG. 11. FIG. 11 is a flow chart illustrating the flow of the update processing. As illustrated in FIG. 11, firstly, the learning apparatus 10 calculates error between areas where shadows have been generated in the generated shadow image and the image of shadow output from the shadow encoder (Step S171). Furthermore, the learning apparatus 10 calculates an NLL of the image of target (Step S172). Subsequently, the learning apparatus 10 calculates reconfigured error between the combined output image and the input image (Step S173).

Furthermore, the learning apparatus 10 calculates a loss function, which is a linear sum of error in the image of shadow, the NLL of the image of target, and the reconfigured error (Step S174). The learning apparatus 10 then updates the model parameters such that the value of the loss function is decreased (Step S175).

Figure 12:
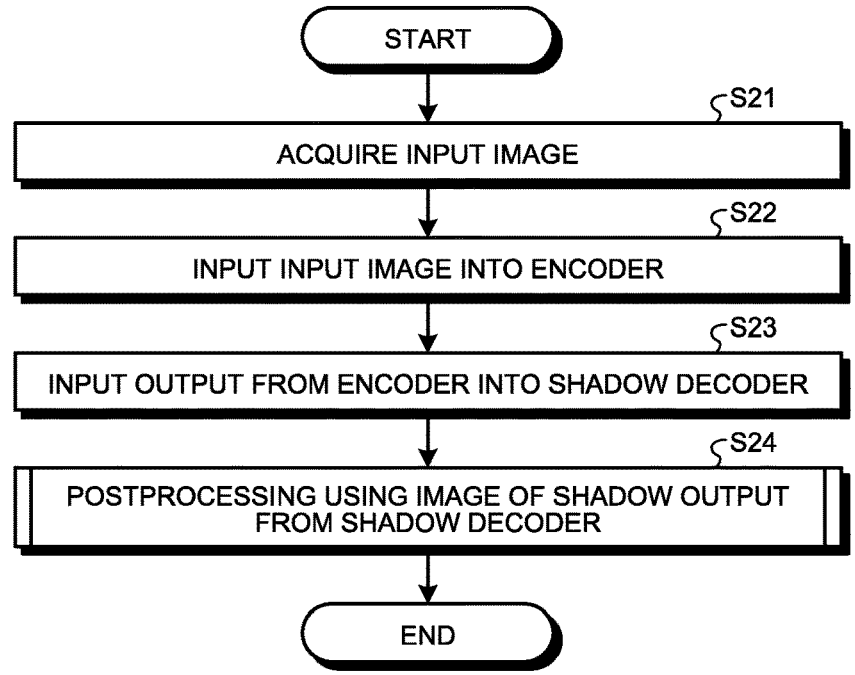
FIG. 12 is a flow chart illustrating a flow of image recognition processing.

A flow of the recognition processing by the recognition apparatus 20 will now be described by use of FIG. 12. FIG. 12 is a flow chart illustrating the flow of recognition processing. As illustrated in FIG. 12, firstly, the recognition apparatus 20 acquires the input image (Step S21), and inputs the acquired input image into the encoder (Step S22). Subsequently, the recognition apparatus 20 inputs the output from the encoder, into the shadow decoder (Step S23). The recognition apparatus 20 then executes postprocessing using the image of shadow output from the shadow decoder (Step S24).

Figure 13:
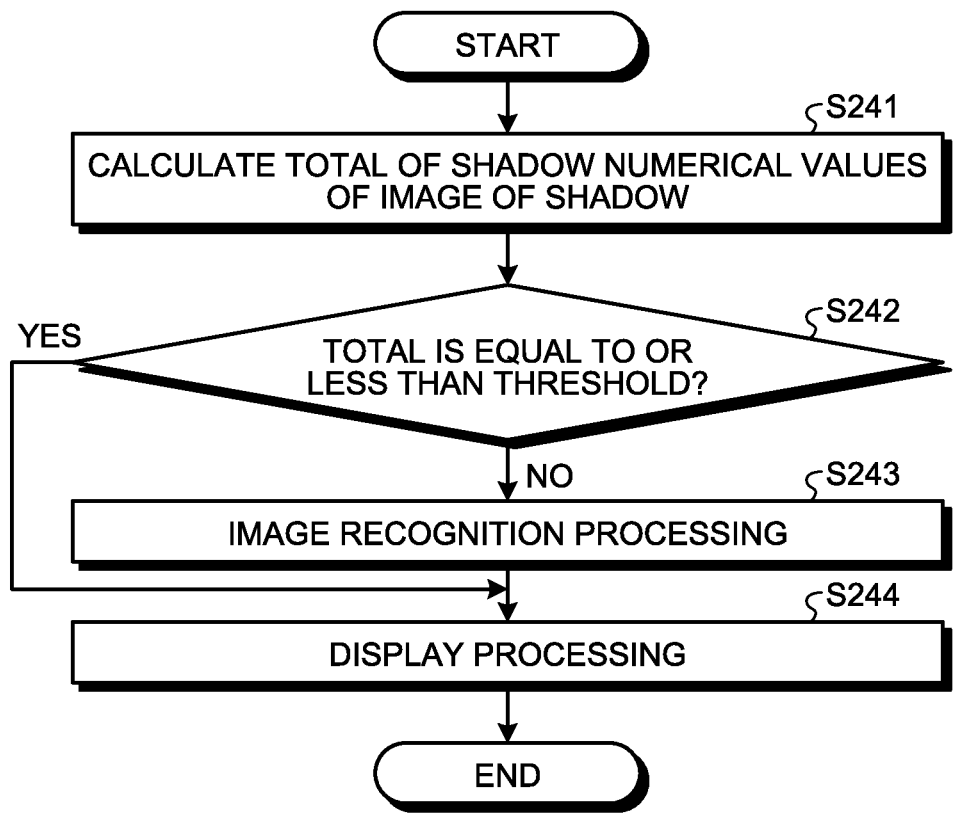
FIG. 13 is a flow chart illustrating a flow of postprocessing.

A flow of the postprocessing at Step S24 will now be described by use of FIG. 13. FIG. 13 is a flow chart illustrating the flow of postprocessing. As illustrated in FIG. 13, firstly, the recognition apparatus 20 calculates the total of shadow numerical values of the image of shadow (Step S241), and determines whether or not the total is equal to or less than a threshold (Step S242).

If the total is not equal to or less than the threshold (Step S242; No), the recognition apparatus 20 determines that no shadow is present, and executes image recognition processing (Step S243). On the contrary, if the total is equal to or less than the threshold (Step S242; Yes), the recognition apparatus 20 determines that a shadow is present, and does not execute image recognition processing.

The recognition apparatus 20 then causes the display device 30 to display the input image (Step S244). Furthermore, if the recognition apparatus 20 has determined that no shadow is present, and has performed image recognition processing, the recognition apparatus 20 causes the display device 30 to display a result of the image recognition processing. On the contrary, if the recognition apparatus 20 has determined that a shadow is present, and has not performed image recognition processing, the recognition apparatus 20 causes the display device 30 to display the image of shadow, together with a message indicating that a shadow is present.

As described above, the learning apparatus 10 generates a shadow image including a shadow corresponding to a state of ultrasound reflection in an input ultrasound image. The learning apparatus 10 inputs an output from the encoder, into which a combined image that is a combination of the input ultrasound image and the shadow image has been input, into the first decoder and the second decoder. Based on reconfigured error, an error function, and a likelihood function, the learning apparatus 10 executes training of the encoder, the first decoder, and the second decoder. The reconfigured error is reconfigured error between: an output image of a coupling function that combines a first image that is an output from the first decoder with a second image that is an output of the second decoder; and the combined image. The error function is an error function between an area in the first image and the shadow in the shadow image, the area corresponding to the shadow in the shadow image. The likelihood function is a likelihood function for the second image, the likelihood function being related to a target in an ultrasound image. As described above, the learning apparatus 10 is able to perform learning, with an automatically generated image of shadow serving as training data. Therefore, according to the embodiment, versatility of determination of presence of any shadow in an ultrasound image is able to be improved.

The learning apparatus 10 executes learning by using a likelihood function having a variable representing a value corresponding to a pixel value of an image, the likelihood function having a maximum value for the variable corresponding to a predetermined pixel value that is neither a maximum pixel value nor a minimum pixel value, the likelihood function being at least one of a first likelihood function and a second likelihood function. Therefore, according to the embodiment, likeness to a target different from the background and shadows is able to be expressed as a likelihood function.

The learning apparatus 10 executes learning by using a likelihood function based on a probability density function of beta distribution having parameters set such that the probability density function has a maximum value when a random variable corresponding to a pixel value of an image is at a predetermined value larger than 0 and smaller than 1, the likelihood function being at least one of the first likelihood function and the second likelihood function. Therefore, by use of pixel values normalized in a range from 0 to 1, likeness to a target different from the background and shadows is able to be expressed as a likelihood function.

According to the above description of the embodiment, the data input to the encoder and the data output from the decoders are both image data, but the input data and output data may be not image data as long as the input data and output data are able to be restored as images. For example, the learning apparatus 10 may treat, as the input data and output data, an ultrasound signal itself acquired from a probe. In this case, the learning apparatus 10 may convert, as needed, data output from the shadow decoder into an image, the data being the ultrasound signal.

Furthermore, in the image processing system 1, the probe 40 may have functions equivalent to those of the recognition apparatus 20. In this case, the probe 40 may determine presence of any shadow in an image of shadow output by use of the shadow decoder from an ultrasound image, and perform notification of a result of the determination through a notification sound.

The processing procedures, control procedures, specific names, and information including various data and parameters, which have been described above and illustrated in the drawings may be arbitrarily modified unless particular mention is made otherwise. Furthermore, the specific examples, distributions, and numerical values described with respect to the embodiment are just examples, and may be arbitrarily modified.

Furthermore, the elements of each device in the drawings have been illustrated functionally and/or conceptually, and do not need to be physically configured as illustrated in the drawings. That is, specific modes of separation and integration related to the devices are not limited to those illustrated in the drawings. That is, all or a part of these devices may be configured by functional or physical separation or integration thereof in any units according to various loads and use situations. Moreover, all or any part of the processing and functions implemented in the devices may be realized by a CPU and a program analyzed and executed by the CPU, or may be realized as hardware by wired logic.

Figure 14:
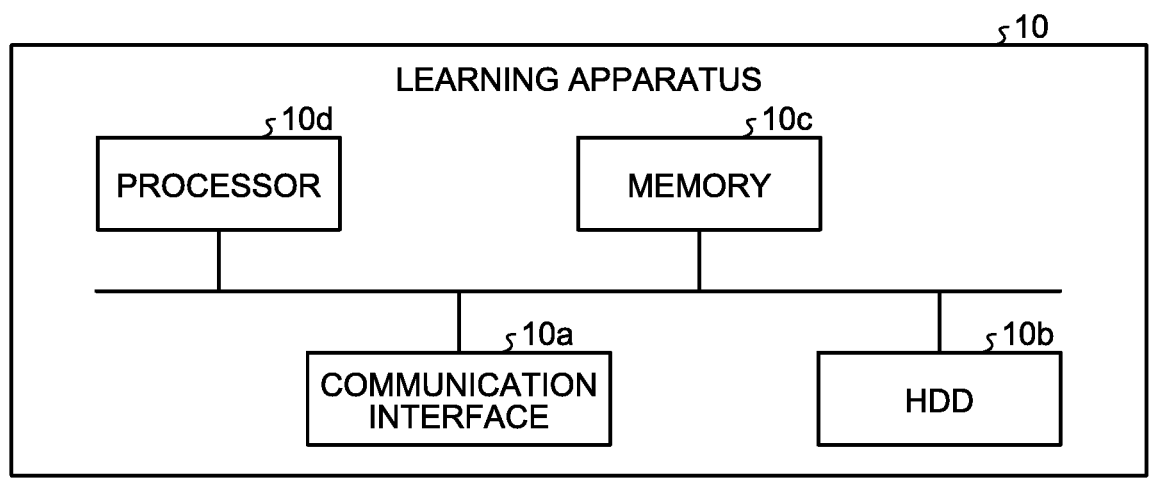
FIG. 14 is a diagram illustrating an example of a hardware configuration.

FIG. 14 is a diagram illustrating an example of a hardware configuration. As illustrated in FIG. 14, the learning apparatus 10 has a communication interface 10a, a hard disk drive (HDD) 10b, a memory 10c, and a processor 10d. Furthermore, these units illustrated in FIG. 14 are connected to one another via a bus.

The communication interface 10a is a network interface card, and performs communication with another server. The HDD 10b stores therein a program that causes the functions illustrated in FIG. 1 to be operated, and a DB.

The processor 10d causes a process to be operated, the process executing the functions described by reference to FIG. 1, by: reading, from the HDD 10b, the program that executes the same processing as the processing units illustrated in FIG. 1; and loading the program into the memory 10c. That is, this process executes the same functions as the processing units included in the learning apparatus 10. Specifically, the processor 10d reads a program having the same functions as the generating unit 130, the input unit 131, the coupling unit 132, and the learning unit 133, from the HDD 10b. The processor 10d then executes the process that executes the same processing as the generating unit 130, the input unit 131, the coupling unit 132, and the learning unit 133. The processor 10d is, for example, a hardware circuit, such as a CPU, an MPU, or an ASIC.

As described above, the learning apparatus 10 operates as an information processing apparatus that executes a learning method, by reading and executing the program. Furthermore, the learning apparatus 10 may realize the same functions as those according to the above described embodiment by reading the program from a recording medium by means of a medium reading device, and executing the program read. The program referred to herein is not limited to being executed by the learning apparatus 10. For example, the present invention may be similarly applied to a case where another computer or a server executes the program, or a case where these computer and server execute the program in corporation with each other.

The program may be distributed via a network, such as the Internet. Furthermore, the program may be executed by being recorded in a computer-readable recording medium, such as a hard disk, a flexible disk (FD), a CD-ROM, a magneto-optical disk (MO), or a digital versatile disc (DVD), and being read from the recording medium by a computer.

According to one aspect, versatility of determination of presence of any shadow in an ultrasound image is able to be improved.

All examples and conditional language provided herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium storing therein a learning program that causes a computer to execute a process comprising:
   generating a shadow image including a shadow according to a state of ultrasound reflection in an ultrasound image;
   generating a combined image by combining the ultrasound image and the shadow image;
   inputting, into a first decoder and a second decoder, an output acquired from an encoder in response to inputting the combined image into the encoder; and
   executing training of the encoder, the first decoder, and the second decoder, based on:
      reconfigured error between an output image of a coupling function and the combined image, the coupling function being configured to combine a first image output from the first decoder with a second image output from the second decoder,
      an error function between an area in the first image and the shadow in the shadow image, the area corresponding to the shadow in the shadow image, and
      a likelihood function related to a likelihood of the second image with respect to an object in the ultrasound image.

2. The non-transitory computer-readable recording medium according to claim 1, wherein the executing learning includes executing learning by using the likelihood function related to a target, the likelihood function being a likelihood function having a variable representing a value corresponding to a pixel value of an image, the likelihood function having a maximum value for the variable corresponding to a predetermined pixel value that is neither a maximum pixel value nor a minimum pixel value.

3. The non-transitory computer-readable recording medium according to claim 1, wherein the likelihood function is a likelihood function based on a probability density function of beta distribution having parameters set such that the probability density function has a maximum value when a random variable corresponding to a pixel value of an image is at a predetermined value larger than 0 and smaller than 1.

4. A learning apparatus comprising:
a memory; and
a processor coupled to the memory and the processor configured to:
  generate a shadow image including a shadow according to a state of ultrasound reflection in an ultrasound image,
  generate a combined image by combining the ultrasound image and the shadow image,
  input, into a first decoder and a second decoder, an output acquired from an encoder in response to inputting the combined image into the encoder, and
  execute training of the encoder, the first decoder, and the second decoder, based on:
    reconfigured error between an output image of a coupling function and the combined image, the coupling function being configured to combine a first image output from the first decoder with a second image output from the second decoder,
    an error function between an area in the first image and the shadow in the shadow image, the area corresponding to the shadow in the shadow image, and
    a likelihood function related to a likelihood of the second image with respect to an object in the ultrasound image.

5. A computer-implemented learning method comprising:
generating a shadow image including a shadow according to a state of ultrasound reflection in an ultrasound image;
generating a combined image by combining the ultrasound image and the shadow image;
inputting, into a first decoder and a second decoder, an output acquired from an encoder in response to inputting the combined image into the encoder; and
executing training of the encoder, the first decoder, and the second decoder, based on:
  reconfigured error between an output image of a coupling function and the combined image, the coupling function being configured to combine a first image output from the first decoder with a second image output from the second decoder,
  an error function between an area in the first image and the shadow in the shadow image, the area corresponding to the shadow in the shadow image, and
  a likelihood function related to a likelihood of the second image with respect to an object in the ultrasound image.

* * * * *